(12) United States Patent
Castelluccio

(10) Patent No.: US 7,560,706 B1
(45) Date of Patent: Jul. 14, 2009

(54) UV GERMICIDE DEVICE FOR COSMETICS AND COSMETIC IMPLEMENTS

(75) Inventor: Daniel Castelluccio, 95 Christopher St., Apt. 6-O, New York, NY (US) 10014

(73) Assignees: Daniel Castelluccio; Cobalt Balloon LLC

( * ) Notice: Subject to any disclaimer, the term of this patent is extended or adjusted under 35 U.S.C. 154(b) by 274 days.

(21) Appl. No.: 11/811,417

(22) Filed: Jun. 7, 2007

Related U.S. Application Data

(60) Provisional application No. 60/811,918, filed on Jun. 8, 2006.

(51) Int. Cl.
*G01N 21/33* (2006.01)
*G01N 21/00* (2006.01)
*A61L 2/10* (2006.01)

(52) U.S. Cl. ............... 250/455.11; 250/454.11; 250/365; 250/504 R; 422/24

(58) Field of Classification Search ........... 250/455.11, 250/454.11, 504 R, 365; 422/24
See application file for complete search history.

(56) References Cited

U.S. PATENT DOCUMENTS

| | | | |
|---|---|---|---|
| 4,255,383 A * | 3/1981 | Schenck | 422/24 |
| 6,766,097 B2 * | 7/2004 | Horton, III | 385/147 |
| 6,962,669 B2 * | 11/2005 | Foreman et al. | 264/1.36 |

* cited by examiner

*Primary Examiner*—Nikita Wells
(74) *Attorney, Agent, or Firm*—Pryor Cashman, LLP; Andrew S. Langsam, Esq.

(57) ABSTRACT

A cosmetics and cosmetic implement germicidal device is provided, having a main housing and an implement support for receiving cosmetics/implements. The support may be a tray or one or more shelves or receptacles. At least one first ultraviolet (UV) bulb is mounted inside the main housing facing the implement support. The UV bulb substantially irradiates a first side of the inner drawer and any cosmetics or implements placed upon the inner drawer. It is preferred to provide UV bulbs on opposite sides of a light-transmissible inner drawer as well as a reflective material inside the main housing so that no portion of any cosmetics or implements remain un-irradiated after use. A single UV bulb that travels or scans may be provided on either side of the drawer, or a number of stationary UV bulbs may be provided, or the implement support may move with respect to the bulbs.

17 Claims, 4 Drawing Sheets

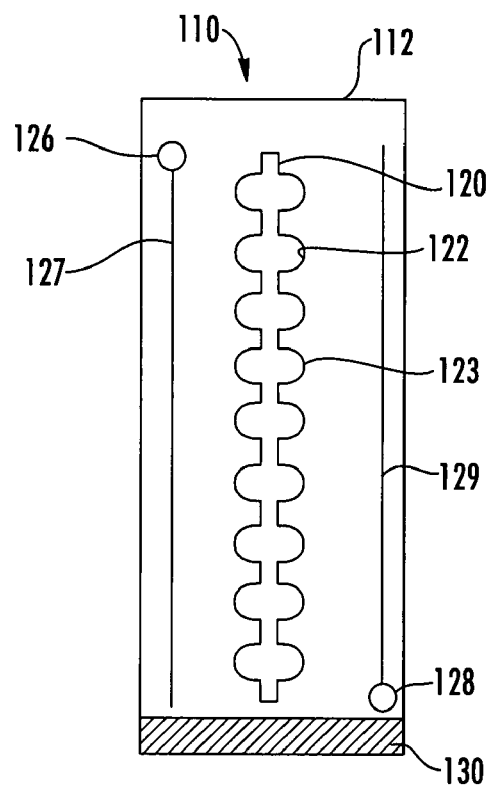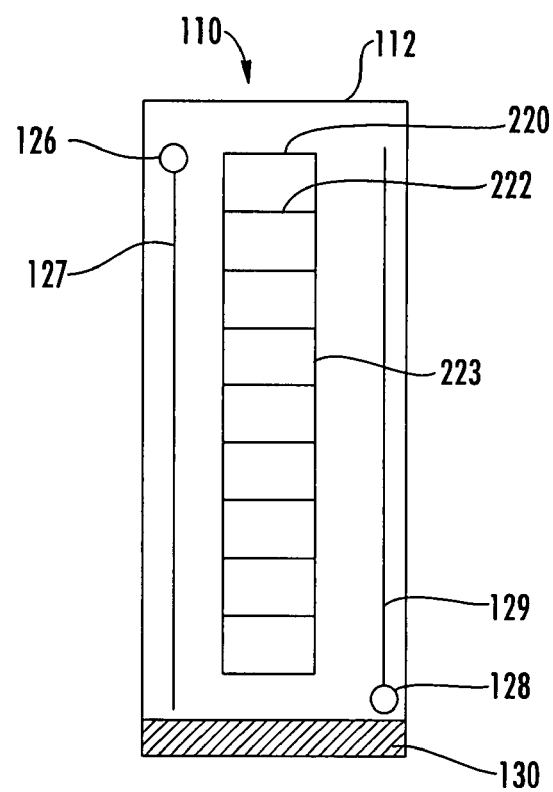
FIG. 6A
FIG. 6B

ID DEVICE FOR COSMETICS
UV GERMICIDE DEVICE FOR COSMETICS AND COSMETIC IMPLEMENTS

RELATED APPLICATION

Domestic priority is claimed from U.S. Provisional Patent Application No. 60/811,918 filed Jun. 8, 2006, entitled "UV Germicide Device for Cosmetic Implements".

BACKGROUND OF THE INVENTION

1. Field of the Invention

The invention relates to cosmetics and cosmetic implements, and more specifically to methods and devices for sanitizing or sterilizing cosmetics and/or cosmetic implements between uses.

2. Description of Related Art

People are increasingly concerned about personal hygiene, i.e. preventing transmission of germs from one person to another. Campaigns to make hand washing more frequent are more prevalent. Sales of instant hand sanitizers such as PURELL® (distributed by Gojo Industries of Akron, Ohio) an anti-bacterial soap, including biocidal agents as triclosan, are on the rise. Recent television reports and newspaper articles have focused on the possibility of "viral or bacterial transmission" in connection with manicures, pedicures and related procedures. Yet there is one place that has avoided scrutiny from a bacterial and viral transmission perspective until now: the department store make-up counter. Everyday, tens if not hundreds of women will sample cosmetics that are on display using the same brush and cosmetic pads without any cleaning of these implements between uses. Any bacteria that is on one user's hands or face will be transmitted to the handle or bristles of the brushes and then to the next user. Additionally, since many of these types of cosmetics are used in close proximity to the eye of the user, bacterial and viral transmission is even more likely owing to the porosity of the eyeball's mucous membrane and surrounding tissues.

In addition to department store cosmetic counters, there are other environments and situations where women may share cosmetics and pick up each other's bacteria and/or viruses. For example, in a dormitory, female (and sometimes male) students often share cosmetics, especially when preparing to go out for an evening. Additionally, even a single user of cosmetics or cosmetics implements may re-infect herself should she have a disease of the eye, treat that disease, then use her unsanitized, germ-riddled cosmetic implements again.

As there has been no method or device yet employed to address this issue, there is a long-felt need in the cosmetics industry to sanitize and/or sterilize cosmetics and cosmetic implements between uses, whether they be by different users or the same user.

SUMMARY OF THE INVENTION

The above and other needs are met by the invention, which is a germicidal device for cosmetics and cosmetic implements. In its most basic form, the device includes a main housing and an implement support, such as a drawer, tray, shelving system, or receptacles, for receiving cosmetics and/or cosmetic implements. At least one first ultraviolet (UV) bulb is disposed on one inner surface of the main housing facing the implement support when the implement support is slid inside the main housing. The UV bulb substantially irradiates a first side of the implement support and any cosmetics or implements placed thereon. It is preferred to provide UV bulbs on opposite sides of a light-transmissible inner drawer as well as a reflective material inside the main housing so that no portion of any cosmetics or implements remain un-irradiated after use. A single UV bulb that travels or scans may be provided on either side of the drawer, or a number of stationary UV bulbs or LEDs may be provided instead. The reflective material may be simply planar or it may focus light from the at least one first UV bulb onto the inner drawer.

The inner drawer may be disposed in a flat configuration and further include a preferably light-transmissible tray made of mesh, lattice, glass, plastic, or the like, or it may be disposed in a vertical configuration and further include a plurality of shelves or similar receptacles adapted to receive cosmetics and/or cosmetic implements. The drawer or tray is preferable adjustable to accommodate a wide variety of different sizes, shapes, and configurations of cosmetics and implements therefor.

In one embodiment, the device includes a main housing with an inner drawer that is slidable into and out of the main housing. The inner drawer includes a removable tray which is light transmissible (mesh, glass, plastic, etc.). Above and below the track for the inner drawer is provided a protective inner screening for preventing any contact between the cosmetics/implements and the other elements of the device. Respectively above and below the protective inner screening are provided at least one (one on each side) UV bulb for irradiation above and below the inner drawer when the inner drawer is slid inside or retracted into the main housing.

In operation, brushes such as eyeliner brushes and mascara brushes, and even small cosmetic items themselves such as lipsticks, compacts, and the like, are placed on the removable tray on top of the inner drawer. Ultraviolet light shines from the ultraviolet bulbs above and below the drawer, killing significant amounts of bacteria or viruses that may be on the brushes or cosmetics, thereby sanitizing or sterilizing the same. Cold cathode UV tubes may be used as the light sources, as may LEDs or any conventional source of UV-C light having a wavelength of preferably less than 280 nm.

In one embodiment, a single tubular UV bulb is provided above the protective screening, and another single UV bulb is provided below the screening. These two bulbs are optionally movable inside the main housing, and during operation of the device, "scan" or travel across the top and bottom of the inner drawer and the tray and anything placed upon it. In this way, no surface of the items to be sanitized or sterilized escapes the sanitizing radiation of the ultraviolet light bulbs.

BRIEF DESCRIPTION OF THE DRAWINGS

FIGS. 6A-B are side sectional views of vertical embodiments of the inventive cosmetic and cosmetic implement sterilizer.

DETAILED DESCRIPTION OF THE EMBODIMENTS AND THE DRAWINGS

Description will now be given with reference to the attached FIGS. 1-9. It should be noted that these figures are exemplary in nature and should in no way serve to limit the scope of the invention, which is defined by the claims appearing hereinbelow.

Figure 1:
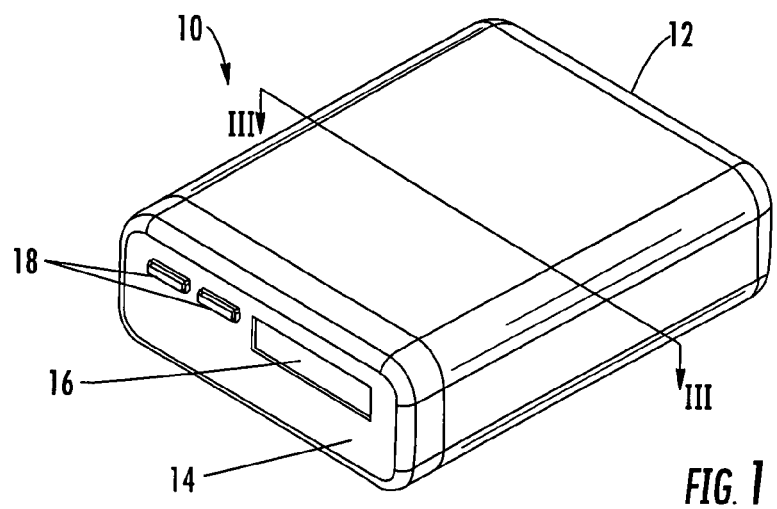
FIG. 1 is a perspective view of one horizontal or flat embodiment of the inventive cosmetic and cosmetic implement sterilizer.
Figure 2A:
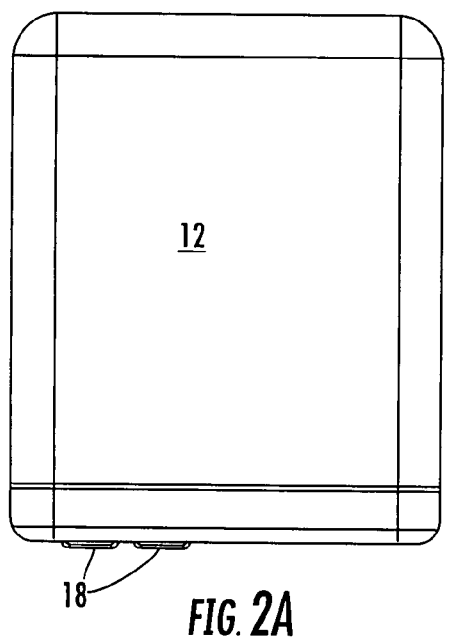
FIG. 2A is a top elevational view of the cosmetic and cosmetic implement sterilizer of FIG. 1.
Figure 2B:
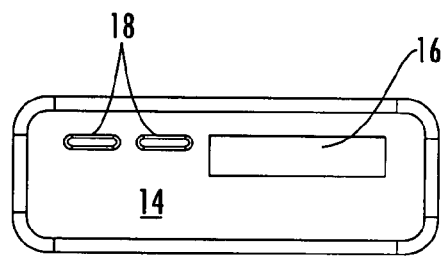
FIG. 2B is a front elevational view of the cosmetic and cosmetic implement sterilizer of FIG. 1.

One embodiment of the inventive sterilization device 10, as shown in FIG. 1, for example, includes a main housing 12 having a front face plate 14. Disposed on face plate 14 is a display 16 and control buttons 18. Display 16 indicates the current state of operation that germicidal device 10 (on, off, working, etc.), and/or it may indicate the amount of time left in the current sterilizing cycle (preferably approximately 30 seconds). Buttons 18 are used to control the operation of the device, e.g., to activate and deactivate the sanitizing operation of the device, possibly to open and close the drawer, and the like. In one embodiment, a single button activates a timed UV cycle of about 30 seconds; the device shuts off when the cycle is finished and may include an audible signal (beep, chime, etc.) to let the user know it is finished.

Figure 3:
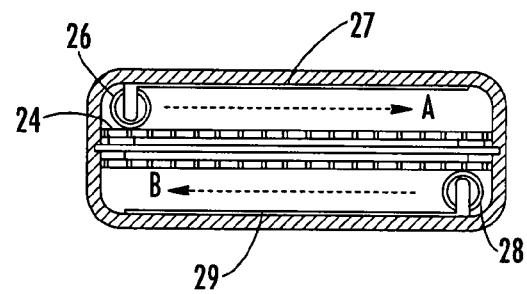
FIG. 3 is a sectional view of the cosmetic and cosmetic implement sterilizer of FIG. 1 taken along line III-III as shown in FIG. 1.
Figure 4:
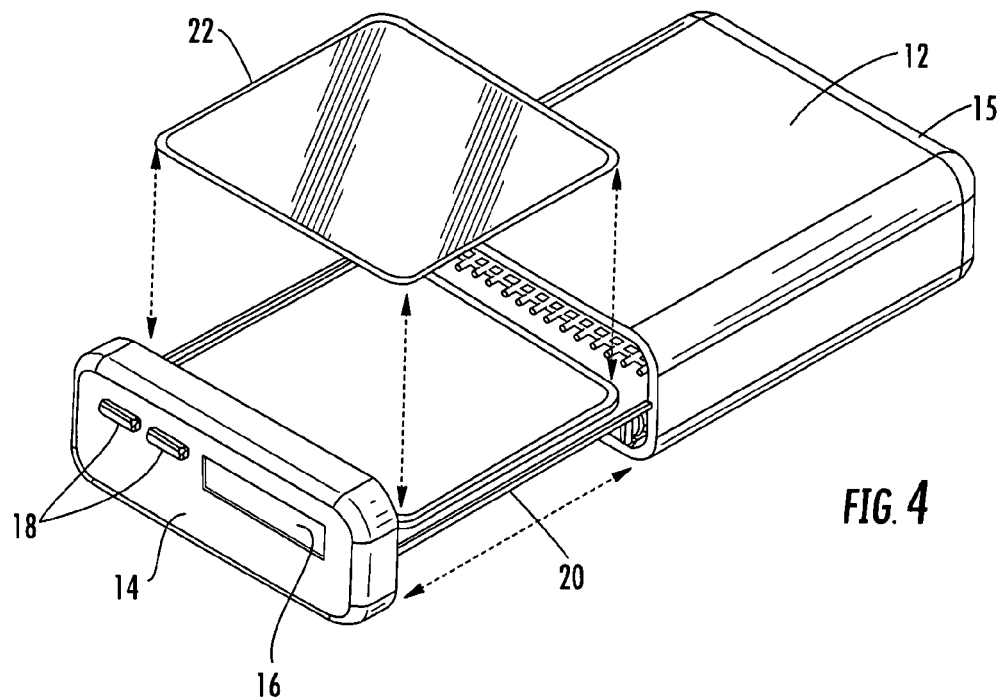
FIG. 4 is a partially exploded perspective view of the cosmetic and cosmetic implement sterilizer of FIG. 1 in its open position.
Figure 5:
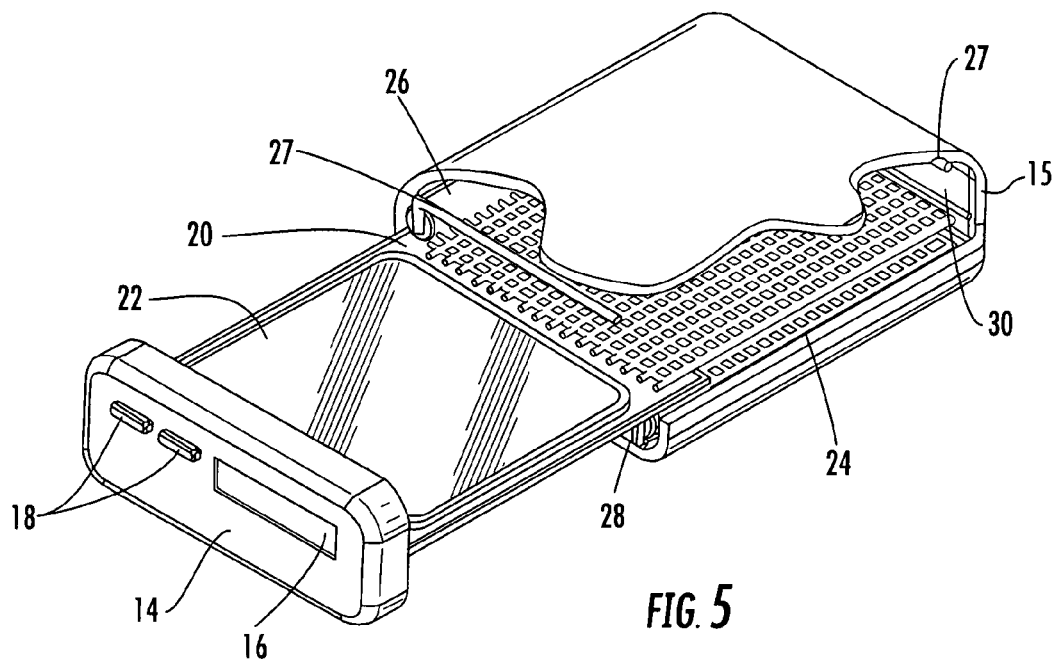
FIG. 5 is a partially cut-away view of the cosmetic and cosmetic implement sterilizer of FIGS. 1-4 noted above.

As best shown in FIGS. 3-5, attached to the inside of face plate 14 is a drawer 20 which includes a removable tray 22 (See FIG. 4). Removable tray 22 is preferably made out of a light transmissible material such as a mesh or glass or plastic that will transmit ultraviolet light. Drawer 20 is slidable on rails into and out of main housing 12, either by manual operation or optionally similar to the mechanized operation of a CD player. Closure may be effected by a spring mechanism, a magnet, a combination thereof, or in a similar manner. Above and below drawer 20 is disposed a protective inner screening 24, best seen in FIG. 5. Inner screening 24 serves to support drawer 20 and protect the UV bulbs from contacting any cosmetics (which might serve to occlude the bulbs and reduce their efficacy). Ultraviolet bulbs 26 (above) and 28 (below) are provided above and below screening 24. While a plurality of UV bulbs may be provided, in the embodiment shown, a single bulb 26 is provided above screening 24 and a single bulb 28 is provided below screening 24. The bulbs extend along the length of the device i.e., from face plate 14 toward back wall 15. Bulb 26 is mounted on a bulb track 27 and is movable by a small motor and pulleys/cord (not shown) in the direction of arrow A as shown in FIG. 3. Similarly, bulb 28 is mounted upon bulb track 29 (see FIG. 3) and is movable in the direction of arrow B as shown in FIG. 3. Preferably, the interior of housing 12 is provided with a lining 30 as shown in FIG. 5. Lining 30, preferably metal, protects the housing (which is preferably plastic) from direct contact with ultraviolet light, which may degrade the integrity of the housing. Lining 30 may also be provided with a reflective surface. The reflective surface may simply be flat or it may be curved or angled to focus the UV light onto a specific location inside the device (e.g., one end of the tray where the bristles of the implements are aligned).

In operation, the invention works as follows. After a person has used a cosmetic brush or other similar implement, it is desirable to have it sterilized. Either the user or the employee at the make-up counter in a department store will open drawer 20 to expose tray 22. Drawer 20 may be opened by pulling on face plate 14, or it may be provided with a spring latch mechanism (not shown), so that pressing on face plate 14 when it is closed causes the drawer to open. A mechanical device similar to that used in a CD player can also be used. In any event, the brushes, implements, and/or cosmetics to be sterilized are placed on tray 22. The drawer is then closed, preferably by pressing on the front of face place 14 to push the drawer inside main housing 12. The device is activated by pressing one (or more) button(s) 18, and UV bulbs 26 and 28 are energized. Power is provided to the device, whether by batteries or a power supply by a cord and plug (not shown). During a sterilization cycle, bulbs 26 and 28 move along their respective bulb tracks 27 and 29 in the directions of arrows A and B shown in FIG. 3 (or stationary bulbs simply remain in a fixed position). In this way, the entire surface of the brushes and other items to be sterilized is irradiated from above and below. The status of the sterilization cycle is displayed on the display 16. When the cycle is completed, the display will indicate as such. In one embodiment, when the sterilization cycle is completed, drawer 20 will automatically open to indicate that the implements and such are clean and ready for re-use.

The invention is not limited to the above description. For example, bulb track 27 and 29 are shown to have two rod-like members (see FIG. 5), however the bulb tracks may employ any number of supports that enable the UV bulbs to move across the interior of this device. Similarly, as shown in FIG. 3, bulb 26 moves from left to right and bulb 28 moves from right to left. It is anticipated that the bulb may move back and forth one or more times during a single sterilization cycle. Similarly, buttons 18 have been described as control buttons that can turn the machine on and off. However, more than two buttons may be provided, and additional functionality may be included, e.g., different settings for different implements, different durations of the sterilization cycle, different power level intensities for the UV bulbs, and the like. Also, the UV bulbs depicted are tubular bulbs, however any convenient size or shape of UV bulb may be employed, even a plurality or a bank of UV LEDs may be employed, as long as they emit the proper wavelength of UV light (i.e., UV-C<280 μm); the term "bulb" is meant to encompass any source of UV-C light. Although it is preferred that tray 22 be removable from drawer 20, it need not be so; instead, tray 22 may be fixed and integral with drawer 20, as long as it is still UV-light transmissible.

Another embodiment is shown in FIGS. 6A-B. The previous embodiment of FIGS. 1-5 was shown in a substantially flat or horizontal configuration, and FIG. 6 depicts a device 110 having an upright or vertical configuration. Vertical device 110 occupies much less countertop space and may be attractive for smaller stores or shops that have cluttered countertops. The majority of the elements are similar: here, UV bulbs 126 and 128 ride along rails 127 and 129 (or similar structure) respectively, and inner drawer 120 slides into and out of main housing 112.

Since the configuration is vertical, however, a simple tray will not suffice to retain implements or cosmetics. In FIG. 6A, vertical inner drawer 120 includes a plurality of longitudinal receptacles 122 which are dimensioned to accept cosmetics (e.g., a tube of lipstick) or implements (e.g., eyeliner brushes). The sidewalls 123 of receptacles are preferably light-transmissible (mesh, glass, plastic, etc.) so that light from UV bulbs 126 and 128 may reach the cosmetics and implements placed therein. In FIG. 6B, vertical inner drawer 220 includes a plurality of horizontal shelves 222 supported by sidewalls 223. Again, sidewalls 223 should be light transmissible; they need not be full walls, as a few vertical supports are likely sufficient to support shelves 222.

In both FIGS. 6A and 6B, ballast 130 is preferably provided in the base of the device to make it less likely to fall over when inadvertently touched or knocked or when the surface upon which device 110 sits otherwise moves.

The UV bulbs in FIG. 6 are shown mounted parallel to the base and scan up and down, but they could also be mounted perpendicular to the base and scan front to back instead.

Figure 7:
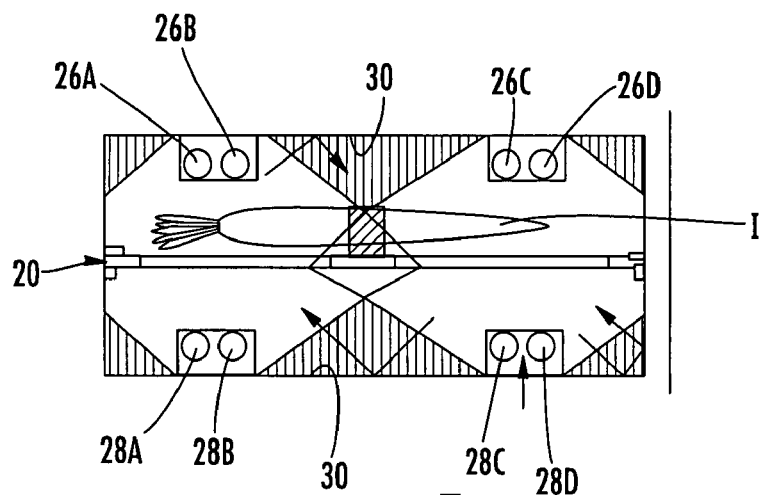
FIG. 7 is a side sectional view of another horizontal embodiment of the inventive cosmetic and cosmetic implement sterilizer having stationary UV bulbs.

FIG. 7 depicts another (horizontal) embodiment of the invention. Like elements are given like reference numerals, and their description will not be repeated. Instead of a single UV bulb mounted above and/or below tray 20, a series of stationary UV bulbs 26A-D are fixedly mounted above tray 20, and a series of stationary UV bulbs 28A-D are fixedly mounted below tray 20. Reflective surface 30 causes light from the bulbs that would otherwise be directed away from implement I on tray 20 to be directed towards implement I.

Figure 8:
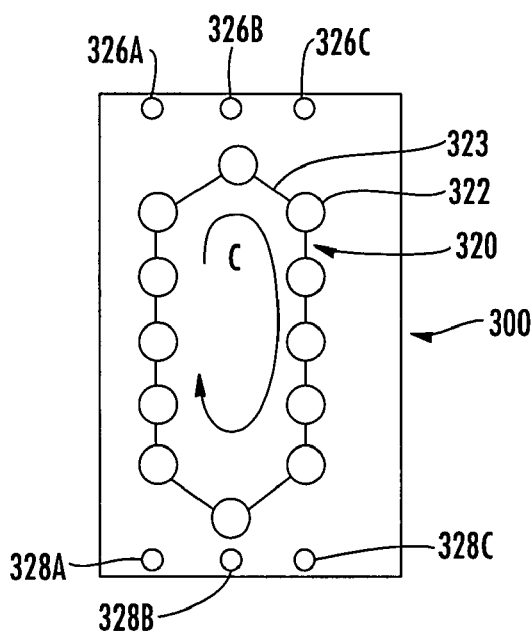
FIG. 8 is a side sectional view of another embodiment of the inventive cosmetic and cosmetic implement sterilizer in which the implement support moves with respect to stationary UV bulbs.

As another alternative, instead of the UV bulbs moving over a stationary tray or drawer, the tray or drawer or other implement support may be caused to move with respect to stationary UV bulbs, preferably in a direction perpendicular to the longitudinal axis of the UV bulbs (if the bulbs have such axes). In the case of a tray or drawer implement support, the tray/drawer may slide along a track. Alternatively, the implement support may be a rotisserie-type rotating support 320 as shown in FIG. 8. Rotating support 320 includes receptacles 322 connected by linkages 323. Receptacles 322 are, as above, preferably light-transmissible. Rotating support rotates in the direction of arrow C (which happens to be clockwise, however the invention works just as well if the support rotates counterclockwise) which brings each receptacle 322 past UV bulbs 326A-C at the top of the device and UV bulbs 328A-C at the bottom of the device. UV bulbs may be mounted on the side walls of device 300 in addition to or in the alternative to the top and bottom-mounted UV bulbs shown in FIG. 8. Specific placement of the UV bulbs with respect to the housing is immaterial.

Figure 9:
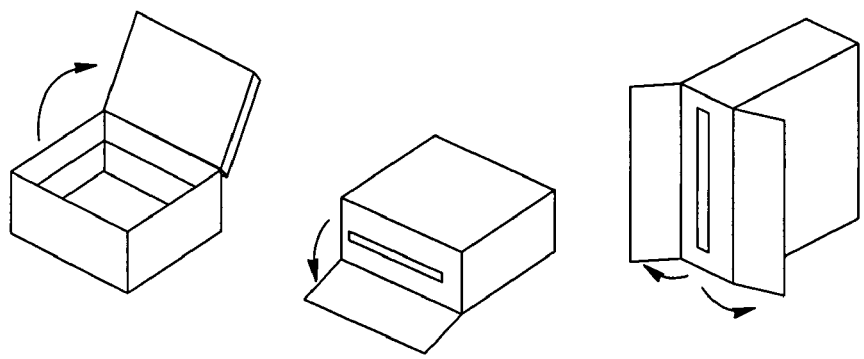
FIG. 9 schematically depicts various alternative housings and openings thereof for the inventive cosmetic and cosmetic implement sterilizer.

FIG. 9 schematically depicts several configurations of the housing for the inventive device, showing a top cover opening, a front face opening, and the like. It is preferred that the door be connected to a kill switch that, when the door is opened, deactivates the UV bulbs so as to prevent injury from exposure to the UV light.

Having described certain embodiments of the invention, it should be understood that the invention is not limited to the above description or the attached exemplary drawings. Rather, the scope of the invention is defined by the claims appearing hereinbelow and any equivalents thereof as would be appreciated by one of ordinary skill in the art.

What is claimed is:

1. A cosmetics and cosmetic implement germicidal device, comprising:
   a main housing;
   an implement support for receiving cosmetics and/or cosmetic implements; and
   at least one first ultraviolet (UV) bulb disposed on a first inner surface of said main housing facing said implement support,
   wherein said at least one first UV bulb substantially irradiates a first side of said implement support and any cosmetics and/or cosmetic implements placed thereon and wherein said implement support further comprises a drawer that slides into and out of said main housing.

2. A cosmetics and cosmetic implement germicidal device according to claim 1, further comprising a reflective material disposed on at least a portion of an inner surface of said main housing.

3. A cosmetics and cosmetic implement germicidal device according to claim 2, wherein said reflective material focuses light from said at least one first UV bulb onto said implement support.

4. A cosmetics and cosmetic implement germicidal device according to claim 1, said drawer further comprising a substantially flat tray.

5. A cosmetics and cosmetic implement germicidal device according to claim 4, wherein said tray is light-transmissible.

6. A cosmetics and cosmetic implement germicidal device according to claim 5, wherein said light-transmissible tray comprises at least one of mesh, lattice, glass, or plastic.

7. A cosmetics and cosmetic implement germicidal device according to claim 1, further comprising at least one second UV bulb disposed on a second inner surface of said main housing opposite said first inner surface and also facing said implement support,
   wherein said at least one second UV bulb substantially irradiates a second side of said implement support and any cosmetics and/or cosmetic implements placed thereon.

8. A cosmetics and cosmetic implement germicidal device according to claim 7, wherein said at least one second UV bulb is movably mounted within said main housing, wherein when said at least one second UV bulb is activated, said at least one second UV bulb moves and scans along said implement support.

9. A cosmetics and cosmetic implement germicidal device according to claim 7, wherein said at least one second UV bulb comprises a plurality of UV bulbs mounted on said second inner surface.

10. A cosmetics and cosmetic implement germicidal device according to claim 1, wherein said at least one first UV bulb is movably mounted within said main housing, and wherein when said at least first UV bulb is activated, said at least one first UV bulb moves and scans along said implement support.

11. A cosmetics and cosmetic implement germicidal device according to claim 10, further comprising at least one second UV bulb disposed on a second inner surface of said main housing opposite said first inner surface and also facing said implement support,
   wherein said at least one second UV bulb substantially irradiates a second side of said implement support and any cosmetics and/or cosmetic implements placed thereon.

12. A cosmetics and cosmetic implement germicidal device according to claim 11, wherein said at least one second UV bulb is movably mounted within said main housing, wherein when said at least one second UV bulb is activated, said at least one second UV bulb moves and scans along said implement support.

13. A cosmetics and cosmetic implement germicidal device according to claim 1, further comprising a protective screening disposed between said at least one first UV bulb and said implement support preventing contact between any items placed on said implement support and said at least one first UV bulb.

14. A cosmetics and cosmetic implement germicidal device according to claim 1, said implement support being disposed in a vertical configuration and further comprising a plurality of shelves adapted to receive cosmetics and/or cosmetic implements.

15. A cosmetics and cosmetic implement germicidal device according to claim 1, wherein said at least one first UV bulb comprises a plurality of UV bulbs mounted on said first inner surface.

16. A cosmetics and cosmetic implement germicidal device according to claim 1, wherein said implement support moved with said cosmetics and/or cosmetic implements with respect to said at least one first UV bulb.

17. A cosmetics and cosmetic implement germicidal device according to claim 16, wherein said implement support further comprises a rotating support having light-transmissible receptacles connected by linkages.

* * * * *